(12) United States Patent
Dasnurkar et al.

(10) Patent No.: US 12,376,860 B2
(45) Date of Patent: Aug. 5, 2025

(54) DEVICES FOR MITIGATING VESSEL LEAKAGE

(71) Applicant: MicroVention, Inc., Aliso Viejo, CA (US)

(72) Inventors: Anup Dasnurkar, Aliso Viejo, CA (US); Maricela Walker, Aliso Viejo, CA (US); Matthew Fitz, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 17/650,364

(22) Filed: Feb. 8, 2022

(65) Prior Publication Data

US 2022/0160367 A1 May 26, 2022

Related U.S. Application Data

(63) Continuation of application No. 16/353,780, filed on Mar. 14, 2019, now Pat. No. 11,272,940.

(60) Provisional application No. 62/644,209, filed on Mar. 16, 2018.

(51) Int. Cl.
 *A61B 17/12* (2006.01)
 *A61F 2/24* (2006.01)
 *A61F 2/90* (2013.01)
 *A61L 31/08* (2006.01)
 *A61L 31/14* (2006.01)
 *A61B 17/00* (2006.01)

(52) U.S. Cl.
 CPC .. *A61B 17/12122* (2013.01); *A61B 17/12118* (2013.01); *A61B 17/1214* (2013.01); *A61B 17/12145* (2013.01); *A61B 17/12168* (2013.01); *A61F 2/2409* (2013.01); *A61F 2/2412* (2013.01); *A61F 2/2418* (2013.01); *A61F 2/246* (2013.01); *A61F 2/90* (2013.01); *A61L 31/08* (2013.01); *A61L 31/145* (2013.01); *A61B 2017/00606* (2013.01); *A61F 2230/0039* (2013.01); *A61F 2250/0007* (2013.01); *A61F 2250/0039* (2013.01); *A61F 2250/0069* (2013.01)

(58) Field of Classification Search
 CPC ........ A61B 17/12122; A61B 17/12118; A61B 17/1214; A61B 17/12145; A61B 17/12168; A61F 2/2409; A61F 2/2418; A61F 2/90
 See application file for complete search history.

(56) References Cited

U.S. PATENT DOCUMENTS

| | | | |
|---|---|---|---|
| 5,725,552 A * | 3/1998 | Kotula | A61B 17/12022 604/509 |
| 10,130,467 B2 | 11/2018 | Braido et al. | |
| 10,271,949 B2 | 4/2019 | Dakin et al. | |
| 2005/0137688 A1 | 6/2005 | Salahieh et al. | |
| 2005/0288706 A1* | 12/2005 | Widomski | A61B 17/0057 606/213 |
| 2006/0004442 A1 | 1/2006 | Spenser et al. | |
| 2007/0265656 A1 | 11/2007 | Amplatz et al. | |
| 2008/0065148 A1 | 3/2008 | Corcoran et al. | |

(Continued)

*Primary Examiner* — Suba Ganesan
(74) *Attorney, Agent, or Firm* — Inskeep IP Group, Inc.

(57) ABSTRACT

Heart valve replacement often involves complications associated with paravalvular leaks. Vascular plug and occlusive devices, as well as heart valves particularly beneficial in treating the phenomenon of paravalvular leaks are described to address this issue.

20 Claims, 11 Drawing Sheets

(56) References Cited

U.S. PATENT DOCUMENTS

| | | | |
|---|---|---|---|
| 2011/0178539 A1* | 7/2011 | Holmes, Jr. | A61B 17/12172 |
| | | | 606/151 |
| 2012/0041550 A1 | 2/2012 | Salahieh et al. | |
| 2014/0277425 A1 | 9/2014 | Dakin | |
| 2014/0303719 A1 | 10/2014 | Cox et al. | |
| 2014/0343602 A1* | 11/2014 | Cox | A61B 17/12113 |
| | | | 606/215 |
| 2016/0278750 A1 | 9/2016 | Akpinar | |

* cited by examiner

DEVICES FOR MITIGATING VESSEL LEAKAGE

RELATED APPLICATIONS

This application is a continuation of and claims priority to U.S. patent application Ser. No. 16/353,780 filed Mar. 14, 2019 entitled Devices For Mitigating Vessel Leakage, which is the nonprovisional of and claims priority to U.S. Provisional Application Ser. No. 62/644,209 filed Mar. 16, 2018 entitled Devices for Mitigating Vessel Leakage, which is hereby incorporated herein by reference in its entirety.

BACKGROUND OF THE INVENTION

Artificial heart valves are commonly used to treat a variety of disease conditions in the heart. There often is a gap that develops between the vessel and the heart valve and blood can flow through this gap thereby avoiding the normal movement through the valve, a phenomenon known as paravalvular leakage. Paravalvular leaks can cause a variety of complications including clots, blood regurgitation, reduced blood flow to particular regions of the body, and heart problems due to the heart pumping harder to circulate blood throughout the body. This gap can develop for a variety of reasons, including irregularities in the shape of the blood vessel, as well as the valve becoming detached due to the high pulsatile pressures associated with this region of the heart.

Most techniques to address this issue involve either surgically reattaching to valve to the vessel or using embolic material to fill this gap. For various reasons, the reattachment procedure often does not work or can introduce additional complications. The use of embolic material is problematic since the shape of the gap can vary, therefore it can be difficult to size embolic material that can fill this area—smaller embolic materials can migrate creating clot complications elsewhere in the vasculature, while larger embolic materials are difficult to conform to the shape of the leakage region.

There is a need for a device that can address paravalvular leakage in a safe manner.

SUMMARY OF THE INVENTION

In one embodiment, a paravalvular leak occlusive device is described. In some embodiments the paravalvular leak occlusive device comprises an occlusive vascular plug that can be placed along an entire portion of a heart valve, or along a selected region of a heart valve to occlude space between the heart valve and a blood vessel.

In one embodiment, the paravalvular leak occlusive device comprises a mesh of one or more metallic wires. In other embodiments, the paravalvular leak device comprises fabric, textiles, or polymers.

In one embodiment, the paravalvular leak occlusive device comprises proximal and distal flanged/enlarged ends and a narrow neck or waist region in between. In one embodiment, the device comprises proximal and distal flanges, and an enlarged region in between. The enlarged region can comprise a number of shapes, including disc shaped, cylindrically shaped, cylindrically recessed, and a cylindrically tapered shape. In one embodiment, the device comprises an adjustment mechanism between the proximal and distal flanges, where the adjustment mechanism can lengthen or contract so that the device can adjust to the geometry of the gap region to occlude the target space. The adjustment mechanism can comprise, for example, a spring, tether, wire, and/or shaped braid. The adjustment mechanism can be in various locations along the device, for instance adjacent one flange, adjacent the other flange, or between the two flanges.

In one embodiment, a method of manufacturing a paravalvular leak occlusive device is described. The method comprises braiding one or more wires over a shaped mandrel to create a plurality of different shaped regions along the length of the device, and heat treating the device to impart a heat set shape comprising a plurality of different shaped regions.

In one embodiment, a method of deploying a paravalvular leak occlusive device is described. The device is delivered through a delivery catheter to the location of an artificial heart valve, and near the location of a gap or space between the artificial heart valve and the blood vessel wall which comprises the paravalvular leak. The device is deployed through the catheter to this gapped region such that the paravalvular device occludes the space between the heart valve and the blood vessel, thereby sealing the paravalvular leak.

In one embodiment, a heart valve is described which utilizes an expansile material, such as hydrogel and/or foam, which expands at the treatment site in order to seal the heart valve against the blood vessel, thereby preventing paravalvular leaks.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION

Figure 1:
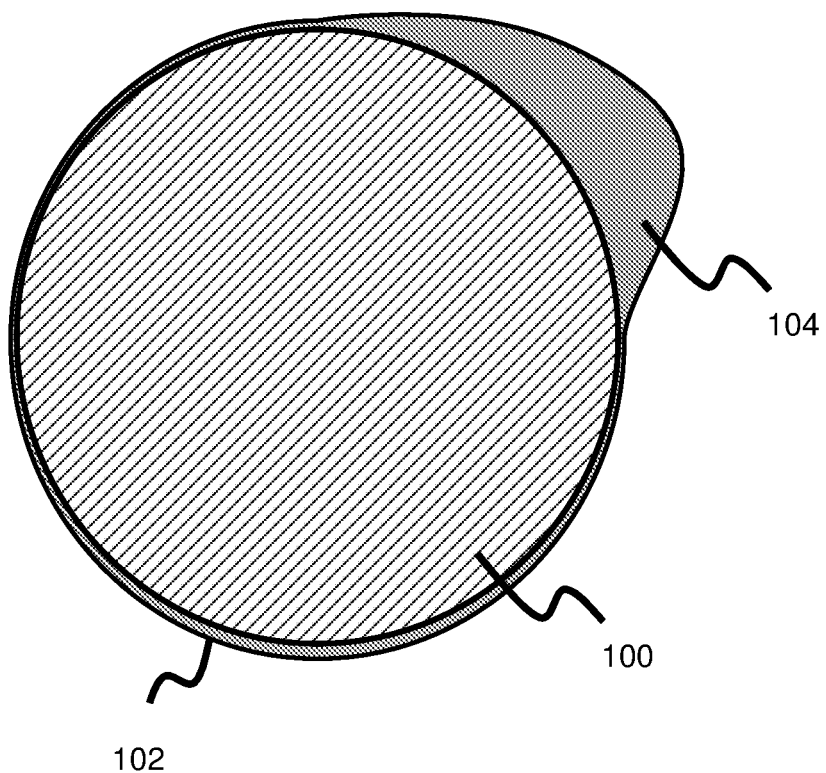
FIGS. 1-3 illustrate a paravalvular leak region between a valve and a vessel.

The human anatomy contains a number of veins and arteries to enable the distribution of blood throughout the body. The arteries send blood to the various regions of the body while the veins return the blood to the heart. The heart is the pump that regulates the flow of blood. The heart includes four valves, these valves function to allow blood to flow through the proper vessels by opening and closing in certain intervals to control blood flow through the heart and throughout the arteries and veins that comprise the body. By opening, the valves allow blood to flow through the valve into the proper artery and by closing the valves prevent backflow through the valves to regulate the flow of blood. These four valves are the tricuspid valve connecting the right ventricle and the right atrium, the pulmonic valve connecting the right ventricle and the pulmonary artery, the mitral valve connecting the left atrium and the left ventricle, and the aortic valve connecting the left ventricle and the aorta.

For various reasons, one or more valves (typically the mitral or aortic valves) can fail to open and/or close properly. Where the valve fails to open properly, less blood gets through the valve which can negatively affect blood flow through the arteries. Where the valve fails to close properly, blood can backflow or leak also causing less blood to flow through the arteries. These issues can cause various problems including heart failure caused by the heart working harder to pump blood, and blood clots, among other complications. Various conditions can cause these valve issues, including stenosis or buildup of calcification, congenital heart defects, anatomical issues where a chamber may be smaller or larger than it should be, and valve leaflets that stretch too much or do not stretch enough.

Valve replacement is one commonly used procedure to treat valve issues; this involves placement of a mechanical or biological (typically animal) heart valve to replace the malfunctioning valve. The valve is often stitched to the surrounding tissue to secure it. The valve can become separated from the surrounding tissue causing gaps to appear between the valve and the surrounding tissue and vessel wall; this separation can occur for a variety of factors including force associated from the pulsatile pressures of the region, and calcification in the vessel wall which makes attachment difficult. Furthermore, the valve implant region can have an irregular shape due to various reasons including a natural irregular shape, and calcification creating an irregularly shaped profile—also leading to the formation of gaps or space between the valve and the vessel. Blood can flow through these gaps, a phenomenon known as paravalvular leakage. This leakage causes issues such as backflow and clotting; additionally, by bypassing the normal flow through the valves, this creates other complications since this interferes with the regulated blood flow enabled by the opening and closing of the valves enable. One approach to dealing with this issue is to reattach the replacement valve to the vessel wall. However, where the vessel wall is calcified thereby causing detachment to occur, reattachment is unlikely to permanently address the issue. Furthermore, this may not be an option in certain patients since this involves an invasive procedure.

The present invention addresses the issue by providing a compliant occlusive plug to fill the space between the valve and the vessel, thereby filling the open space which would otherwise allow blood to bypass the valves. By filling this space, the occlusive device/occlusive plug restores normal flow through the valve, thereby avoiding the various complications described above.

Figure 2:
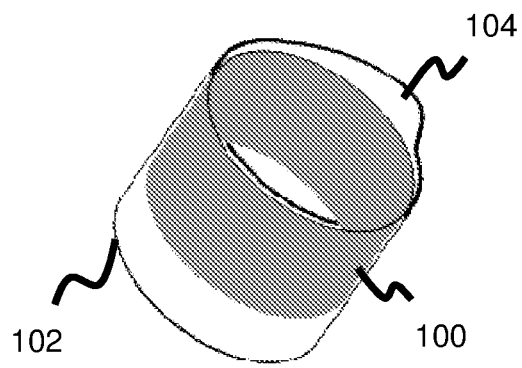
Figure 3:
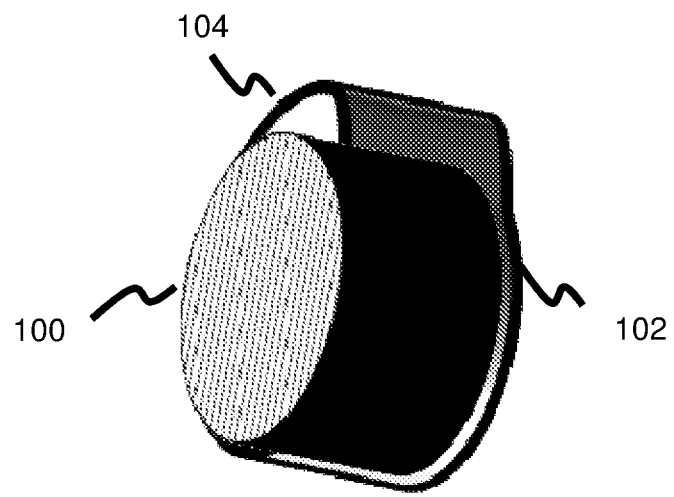

FIG. 1 illustrates a cross-sectional view of a valve 100 within a larger blood vessel 102 and a gap 104 between the valve and the blood vessel. Due to the presence of this gap 104, some blood is diverted away from the valve affecting the normal circulation of blood. The gap 104 can form for a variety of reasons discussed earlier, including a portion of the valve becoming unattached to the vessel. The vessel often has a disproportionate shape, and the region experiences high turbidity due to the relatively strong blood flow in the heart—factors that can contribute to the gap formation between the valve and vessel. A multi-dimensional view of this cross-section of FIG. 1 is shown in FIGS. 2 and 3, including gap 104 which extends for a length between valve 100 and blood vessel 102. For ease of illustration, the actual valve itself (the mechanical gate that opens and closes to regulate the flow of blood) is not illustratively shown on valve 100.

Figure 4:
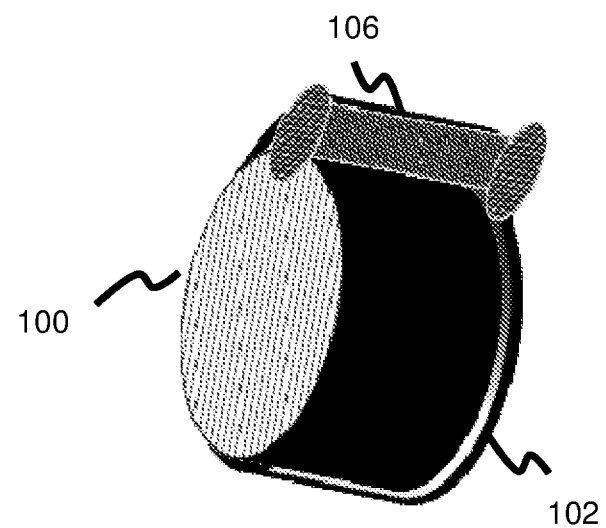
FIG. 4 illustrates a paravalvular leak occlusive device sealing a paravalvular leak region, according to one embodiment.
Figure 5:
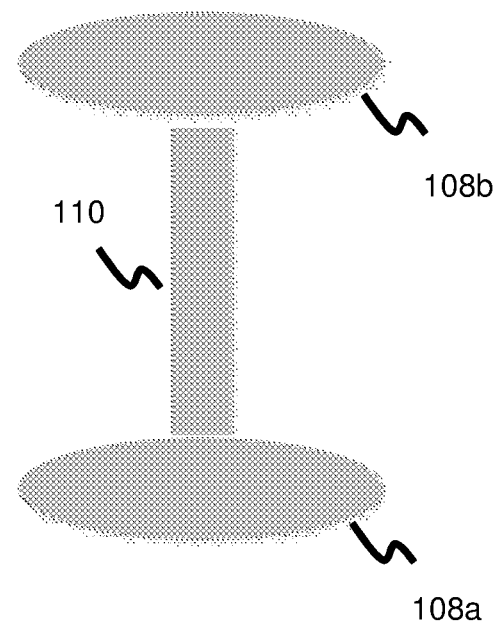
FIG. 5 illustrates a paravalvular leak occlusive device, according to one embodiment.

The present inventive embodiments relate to a compliant occlusive device that is placed across this gap region to occlude the gap and thereby address the issue of paravalvular leakage. Once this gap region is occluded, blood cannot bypass the valve and therefore normal blood flow through the valve is restored. FIG. 4 shows, by way of illustrative example, how the proposed paravalvular leak occlusive device 106 would be positioned relative to valve 100 and vessel 102, in order to occlude the gap 104. The occlusive device shown 106 has two flanged/enlarged ends 180a and 180b and a narrow waist region 110 in between—this is shown in more detail in FIG. 5. The enlarged ends help to ensure blood cannot get within the gap region 104, while the narrower waist region actually sits within the gap to occlude it.

In one embodiment, the paravalvular occlusive device is comprised of a braid of one or more metallic wires (e.g., nitinol, stainless steel, cobalt chromium, or other metals). The paravalvular occlusive device is preferably wound with good shape memory material such as nitinol. To aid in visibility, the device can also include radiopaque wires (e.g., tantalum, platinum, palladium, gold) wound into the shape memory metal wire mesh. Other options to augment visibility include the use of drawn-filled tubing or DFT which utilizes a non-radiopaque (e.g., nitinol) outer jacket surrounding an inner radiopaque core material (e.g., tantalum). In other embodiments, polymers or textile fabrics can be used to create the paravalvular leak occlusive device.

The wire braid (or specifically, the waist region 110) is preferably wound in a loose manner to allow the occlusive device to stretch or contract, as needed, to conform to the geometry of the gap since the enlarged ends 180a and 180b should preferentially abut the two ends of the gap itself to prevent an entrance path for blood. In this manner, the looseness of the braid in waist region 110 can act like adjustment mechanism to adjust the overall length of the device and the distance between the two enlarged ends. However, since looser wire braids may sacrifice occlusive effect, a physician can also use visualization and/or other techniques to approximately measure the size of this gap (or derive this information from the length of the plug itself since its likely in some cases, which will be discussed later, that the gap will span the entirety of the valve). In this type of circumstance, a tighter braid pattern can be used where the occlusive device size is customized to reflect the size of the paravalvular leak region and associated gap. Alternatively, since the size of the heart valve is known, the paravalvular occlusive plug can be sized to the dimension of the heart valve since in many circumstances the gap region between the valve and adjacent tissue will span most of or all of the length of the heart valve.

The compliant nature of the device will help the occlusive device fit to the gap/leakage region even with the enlarged ends. It is possible that the flanged/enlarged ends 108a and 108b in their expanded heat set shape will have a larger diameter than the gap 104. However, due to the compliant nature of the device (as well as the compliant nature of the enlarged ends), this will not affect tracking of the occlusive device through this gap region. The proximally located enlarged/flanged end will always sit abutting the gap region and preferably does not physically enter the gap since the proximal enlarged end provides the proximal seal. The rest of the device (including the distal flanged end) is inserted through the gap and tracks through the gap as the user exerts pushing force on the occlusive device during deployment until the distal enlarged end proceeds out of the distal end of the gap. In this way, the flanged ends now sit on either end of the gap helping to occlude the gap, while the middle of the gap forming the paravalvular leak region is occluded by the waist region 110 of the occlusive device.

Flanged/enlarged end regions 108a, 108b can have a variety of shapes, such as elliptical, rectangular, rounded-rectangular, circular. The occlusive device is manufactured by utilizing a mandrel where the mandrel has different shaped sections corresponding to the shape of the flanged and waist sections. In the occlusive device of FIG. 5, by way of example, the mandrel would have two flanged end sections and a narrower waist region in between, which the wires are wound over to form the shape of the occlusive device. The occlusive device is then heat set over the mandrel to impart shape memory into the device. The occlusive device will adopt a first, compressed shape when delivered through a delivery catheter and a second, expanded shape (shown in FIG. 5) when delivered from the catheter and placed at the target region as a result of this imparted shape memory.

Figure 6:
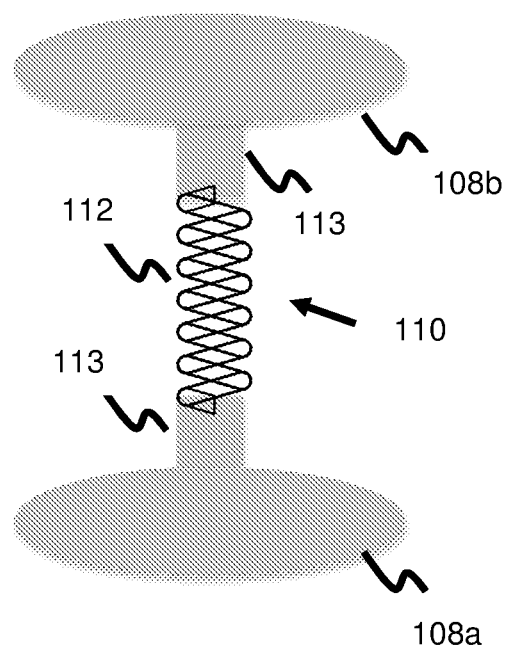
FIG. 6 illustrates a paravalvular leak occlusive device with a spring adjustment mechanism, according to one embodiment.

Several other embodiments can utilize configurations to allow more flexibility of the waist region 110 so that this waist region shortens or lengthens as needed to fit the shape of the gap between the valve and the blood vessel. These embodiments can include an adjustment mechanism 112 to adjust the length of the waist region. As waist region 100 shortens, flanged/enlarged ends 108a and 108b will get closer together; and as waist region lengthens 110, flanged ends 108a and 108b will get further apart. In this way, a one size fits all occlusive device can be utilized which will conform to the length and breadth of the gap to occlude the target area. In one embodiment, the waist region 110 includes an adjustment mechanism 112 which takes the form of a spring, for all or a portion of the length of the waist region—as shown in FIG. 6. In this embodiment, when the device is placed relative to gap 104 (as shown in FIG. 4), the spring would apply a compressive force to the device to bring the flanged ends closer together until the two flanges are sealed against the openings of the gap. In practicality, as will be explained later, a mechanical pusher connects to the proximal flange at the proximal end of the device, as such the proximal flange (e.g., 108b) will likely abut the gap region 104, while the rest of the device is delivered through and out of the gap—at this point, the distal flange will then proximally adjust to seal the other end of the gap, due to the force from the adjustment mechanism 112.

As shown in FIG. 6, the enlarged ends can include an inwardly extending mesh surface 113 and the spring is attached to the inwardly extending surface through a variety of means such as welding or adhesive. The end of the inwardly extending surface can also comprise a marker band or a receiving surface with an engagement element (such as a hole) which a hooked mechanism on the spring engages with to connect the spring to the surface. In another embodiment, there is no inwardly extending surface 113. Rather, a marker band or other receiving surface is at the inwardly facing end of each flanged end 108a, 108b. The spring is then directly attached to the receiving surface. The spring (or a plurality of springs) can be located in various positions along the occlusive device, for instance in between the two enlarged ends or closer to one of the enlarged ends.

In another embodiment, the adjustment mechanism 112 comprises the same mesh of wires that make up the rest of the occlusive device, however the waist region (or a portion of the waist region) section of the device is manufactured in an accordion-like shape comprising folded or compressed regions. In this manner, the adjustment mechanism still comprises the same braid wires as the rest of the device; however, the occlusive device compresses as the adjustment mechanism (here, in the form of the waist region which can adopt an accordion-like folded shape) compresses and elongates as the adjustment mechanism also elongates (like an accordion). Thus, the waist region of the occlusive device which has the folded/compressed/accordion-like shape is the adjustment mechanism. The adjustment mechanism portion of the occlusive device is heat set into its compressed, accordion-like shape. Since the compressed, accordion-like shape is built in as part of its shape memory, the occlusive device will be predisposed to adopting this heat set shape when implanted at the treatment site, thereby enabling the two flanged ends 108a, 108b abut the gapped region to seal or occlude the gapped region. The accordion-shaped adjustment mechanism region will then physically sit within the gap region 104 to occlude this site, while the enlarged/flanged ends 108a, 108b abut the ends of the gap region 104.

Figure 7:
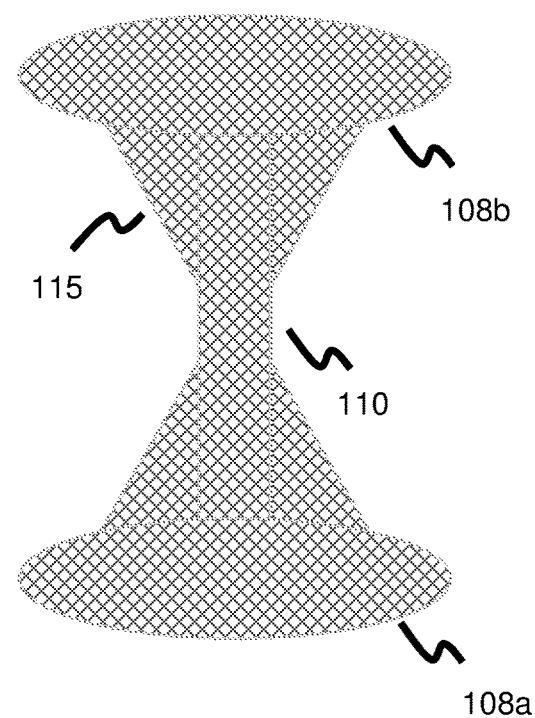
FIG. 7 illustrates a paravalvular leak occlusive device with a tapered waist region, according to one embodiment.

In one embodiment, the medial waist region 110 utilizes a trumpeted or flared profile 115 as shown in FIG. 7. Where the waist region functions as an adjustment mechanism, then as the device compresses, the trumpeted profile will augment the occlusive effect of the waist region of the device (which as discussed earlier, will actually sit along a length of the gap, and therefore occlude the gap). Even where the waist region does not function as an adjustment mechanism (meaning where the device adopts a more or less fixed profile and the flared ends do not inwardly adjust relative to each other), the trumpeted or flared part of the waist region will still augment the occlusive profile of the waist in the area near the flared ends 108a, 108b. The region of the occlusive device near flared ends 108a, 108b is important since that region abuts the gap entrance when implanted, and therefore it is important that occlusion is particularly effective in this location to limit the amount of blood that can enter the gap.

In some embodiments, the waist region 110 is not wound inclusively along with the rest of the occlusive device as in previously discussed embodiments. Instead, the waist region 110 is a separate element which is created/manufactured separately from the rest of the device and is later mechanically attached to the flanged ends 108a, 108b, instead of being wound inclusively of the rest of the occlusive device. This will allow the device to have some independence in performing occlusion, where each section of the paravalvular leak occlusive device can conform to the shape of the section it is meant to cover. The mesh comprising the waist region is attached to the flanged ends 108a, 108b. In one example, the flanged ends 108a, 108b include an attachment component such as a marker band which the wires of the flanged ends are connected to. The marker band further serves as attachment junction for the wires comprising the separate waist region 110. In this manner, the occlusive device is comprised of three sections—flanged end 108a is a first section formed of one braid of wires, flanged end 108b is a second section formed of a second braid of wires, and waist region 110 is a third section formed of a third braid of wires. The three sections are connected together via the tubular marker elements, where the wires from each section are attached to the marker element, for instance by adhesive or welding.

In other embodiments, the adjustment mechanism 112 is a mechanical screw or ratchet mechanism. The screw or ratchet mechanism can adjust in a number of different ways; in one example, the screw or ratchet system is loosely configured to allow for automatic adjustment. For instance, the distal portion of the device (e.g., the portion of the device closer to flange 108a) contains a female groove loosely configured to engage a male mating portion on adjustment mechanism 112 so that the occlusive device self-adjusts over the adjustment mechanism as the occlusive device is positioned relative to the gap between the valve and the vessel.

Figure 8A:
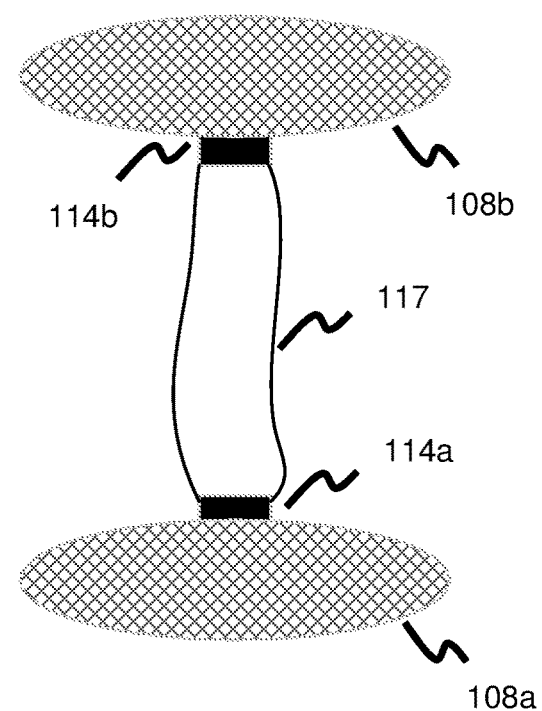
FIG. 8a illustrates a paravalvular leak occlusive device with a waist connection element, according to one embodiment.

In another embodiment, an elongate element 117 such as a tether, thin wire, coil or spring can be used as an adjustment mechanism, as represented in FIG. 8a. Holding elements 114a and 114b are connected to flanged ends 108a and 108b. One or more tethers (e.g., polymer such as PTFE or PTE), thin wires (e.g., nitinol or a radiopaque substance such as tantalum to aid in visualization), or coil/springs are connected with one end attached to one holding element 114a and the other end attached to the other holding element 114b. In one example, the holding elements 114a, 114b take the form of a radiopaque marker band. The holding elements can be attached to the enlarged/flanged ends 108a, 108b in a number of different ways, for instance by welding, adhesive, or other mechanical means. In one attachment technique, the end of each flanged end 108a, 108b includes a male projecting element and the holding element 114a, 114b includes a female receiving element which engages with the male projecting element to connect the holding element to the flanged end. This can be done in a screw-type engagement, or the male projecting element and female receiving element can be welded or otherwise attached together.

Figure 8B:
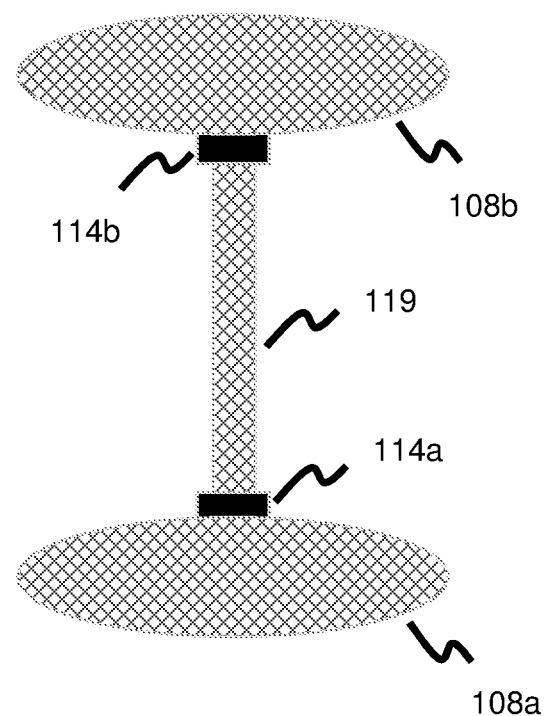
FIG. 8b illustrates a paravalvular leak occlusive device with a waist connection element and a tubular waist, according to one embodiment.

In another similar embodiment shown in FIG. 8b, the occlusive device is formed of three separate but connected elements, including two flanged ends 108a and 108b with a marker band 114a/114b connection at each end. A separately manufactured tubular braid 119 is between the two flanged ends and forms the waist region of the device. The lumen of the tubular marker bands contains a recess and the wire ends of the braided wires comprising the connected flanged end and the connected tubular braid are connected to the marker band, for instance by welding, ties or adhesive. Therefore, tubular marker 114a would connect to the braid comprising flanged end 108a such that the wire ends of the flanged end sit within the marker, and also connect to one end of the tubular braid 119 such that the wire ends of the tubular braid 119 sit within the marker. Marker 114b is configured similarly, except the connection point is between flanged end 108b and tubular braid 119. The device of this embodiment is manufactured by first creating a first enlarged end with a first braid of wires, then next creating a separate second enlarged end with a second braid of wires, then creating a separate waist region with a third braid of wires. These three separate elements are then combined/attached together in the manner described above in this paragraph.

In other embodiments where the tubular braid forming the paravalvular occlusive device is formed of one integral braid, these marker band/holding elements 114a, 114b are used to create the thinner profile of the medial waist region. The wires comprising flanged end 108b are wound through the thinner adjoining marker band 114b and then wound into the thinner waist region. The wires are subsequently pulled through marker band 114a and then wound into the enlarged flanged end region 108b. In this way, the marker bands 114, 114b act as a conduit to bridge sections of a varied shape profile which are produce from a common set of braided wires.

Figure 9A:
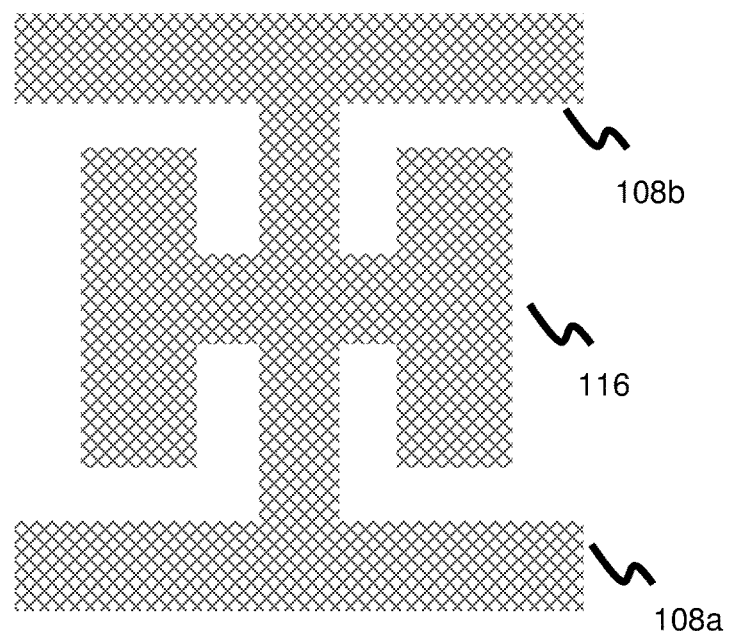
FIG. 9a illustrates a paravalvular leak occlusive device with an enlarged waist region, according to one embodiment.
Figure 9B:
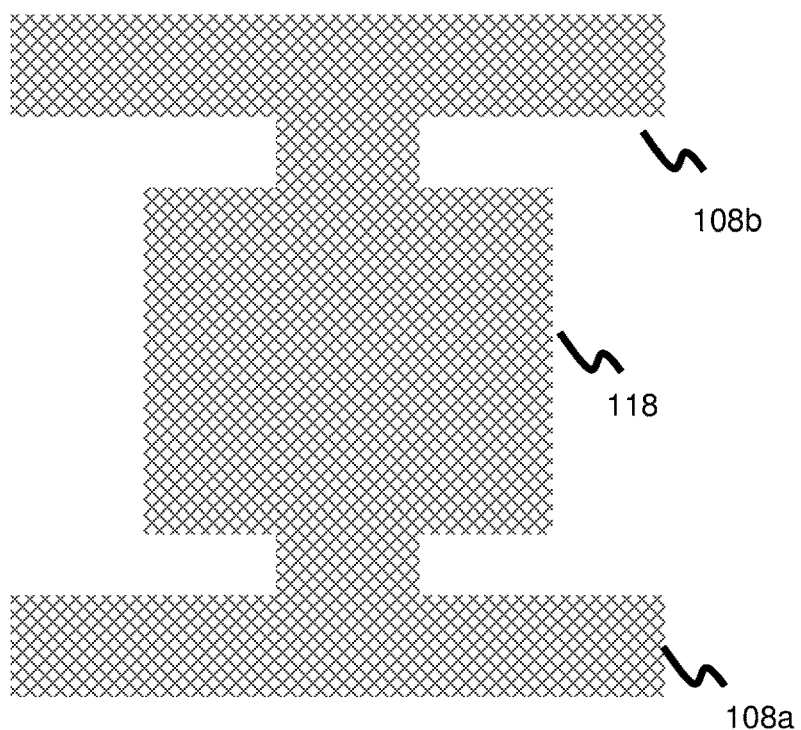
FIG. 9b illustrates a paravalvular leak occlusive device with an enlarged waist region, according to one embodiment.

Other embodiments can utilize a fuller profile along the medial waist region of the occlusive device to augment the occlusive profile along the waist region, as shown in FIGS. 9a and 9b, which utilize wider waist regions 116 and 118. The occlusive device is configured such that as the occlusive device elongates, the waist region thins. Correspondingly, as the occlusive device compresses, the waist region widens. In FIG. 9a, the waist region 116 has a configuration involving a thinner central portion and an enlarged branched region connected to this thinner central portion, forming an H-shape. In FIG. 9b, the waist region includes an enlarged cylindrical type shape profile. The enlarged waist regions 116, 118 can form a variety of shapes. As in the previous embodiments, the two flared end regions 108a, 108b have an elliptical type shape, though other shapes can also be used.

Other embodiments utilize a connecting element connecting one flange (e.g., flange 108b) to the rest of the device. The idea is to allow the majority of the device to float with respect to the one flanged end, allowing more freedom in customizing the rest of the device to fit the target occlusion region of interest. These embodiments would utilize a marker band or other connecting mechanism connected to one of the flanged ends (e.g., flanged end 108b), where the one flanged end is manufactured separately. The rest of the device (e.g., the waist region and other flanged end 108a) is separately manufactured and connected (for example, by welding, adhesive, mechanical ties, etc.) to the connecting mechanism to form one occlusive device. With this approach, the majority of the occlusive device has a certain degree of freedom of movement with respect to the one flanged end, allowing the device freedom in customizing its shape to the target treatment gap region.

Figure 10:
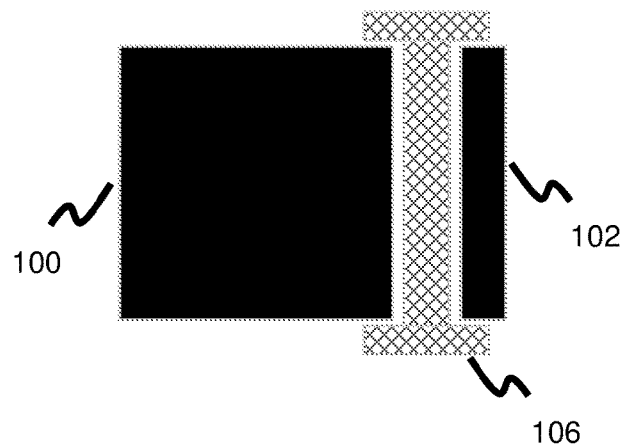
FIG. 10 illustrates a paravalvular leak gap region of a first shape, according to one embodiment.
Figure 11:
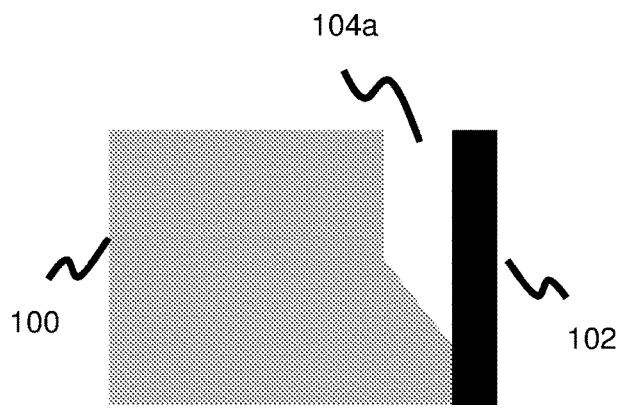
FIG. 11 illustrates a paravalvular leak gap region of a second shape, according to one embodiment.

The occlusive device embodiments discussed so far utilize two flanged ends 108a, 108b at opposing ends of the device. Such embodiments are useful to fill a gap/region where the gap extends along the entire length of the valve, as shown in FIG. 10 where a gap along the entire length of valve 100 is sealed with occlusive plug 106 to seal a gap between valve 100 and tissue/vessel 102. However, in some cases as shown in FIG. 11, the gap extends only along a partial length of the valve but not along the entire length of the valve. For instance, the valve is sutured to the blood vessel but only some of the sutures rupture or detach so that part of the valve is still attached to the vessel. In this situation there might be a proximal gap opening extending into the gap, but there is no gap exit since the other region of the valve is still attached to the tissue. With this type of situation, utilizing an occlusive device with two flanged ends is not necessarily useful since the flange is only needed to seal the opening, while the rest of the device would fill the space (in other words, there is no gap "exit", only a gap "entrance"). This configuration is shown in FIG. 11, where gap 104a only extends along a portion of valve 100 and a portion of the valve remains attached to vessel 102. With this particular gap configuration, the illustrative device embodiments shown in FIGS. 5-9b can be used, except the more distal flange element (e.g., enlarged/flanged end 108a) is omitted. As such, only a proximal flanged end (e.g., enlarged/flanged end 108b) is used, while the rest of the device comprises the occlusive structure that will sit within the gap thereby occluding the gap. Alternatively, where the distal flanged end (e.g., enlarged/flanged end 108a) is highly compliant, the embodiments in FIG. 5-9b can still be used to occlude the type of gap shape region 104a shown in FIG. 11.

Several embodiments have disclosed the use of a connection mechanism or tubular/marker band component placed in a variety of locations along the occlusive device. For instance, the embodiments of FIGS. 8a and 8b show/discuss the use of a tubular marker band as a bridging medium between the flanged/enlarged ends 108a, 108b of the occlusive device and a medial portion between the two enlarged ends. The marker band(s) can be placed along an end region of the flanged/enlarged end or can be placed in a recess created along the flanged end. This recess can be thought of as an inwardly extending dimple. In one embodiment, the tubular marker band can be placed at the proximal and distal ends of the occlusive device such that there is a marker band at each end of the device (in other words, one band at/near the "top" of the device along the top part of flange 108b in the context of the various embodiment figures, and one at/near the "bottom" of the device along the bottom of flange 108a in that context). In the context of this particular embodiment, the tubular band would represent a common connection point for the wires of a particular part of the flanged end of the device, where the wires of that particular region would connect to the internal or external surface of the band. The marker band could either be a projecting surface from the "top" and "bottom" of the device, thereby defining the proximal and distal ends of the occlusive device. Alternatively, the marker bands could sit along an inward dimple created in the surface of the flanged ends 108a, 108b.

Though the primary use of the paravalvular leakage occlusive devices/plugs described to this point have been to occlude the space between the heart valve and adjoining tissue/vessels, these concepts can also be used as a general occlusive device or vascular plug used to occlude a blood vessel, or used to occlude a target region such as an aneurysm, fistula, left atrial appendage, and/or other vascular conditions.

The method of implanting the paravalvular occlusive device will now be described. After implantation of the replacement valve, the physician can use a variety of means (such as imaging, heart murmurs, irregular beating, etc.) to deduce that a paravalvular leak is present. A catheter is tracked up the femoral artery to the target region of the heart, adjacent the valve and specifically at the location of the paravalvular leak. A guidewire is typically used to track the catheter through the vascular system, where the catheter is tracked over this smaller guidewire to the target region. The target placement location could be on either side of the paravalvular leak, depending on factors such as the size of the gap between the valve and vessel associated with the leak and ease of placing/tracking the catheter. Utilizing imaging (e.g., radiography), the paravalvular leak occlusive device is subsequently tracked through and out of the catheter into the treatment location at the valve. In some embodiments, as explained above, the device is sized for the particular target area and in other embodiments the device has a general size that is compliant and fits a wide array of gap sizes/configurations. The paravalvular occlusive device is proximally connected to a mechanical pusher, and the physician controls the device placement through this mechanical pusher. The pusher utilizes detachment means (mechanical (e.g., screw), thermal, and/or electrolytic) which are well known in the art in order to detach the pusher when the paravalvular occlusive device is in the proper location. The pusher should have enough strength to communicate the proximal placement force to the device, especially since this is a very high blood flow region and the associated turbidity is high. At the same time, the pusher should also have a relatively small profile to fit in the catheter while being able to communicate torqueing force as the device is manipulated into its proper location. To this end, the proximal portion of the pusher can utilize stiff materials while the distal portion of the pusher utilizes more flexible materials. Various combinations of metallic materials (e.g., nitinol, stainless steel) as well as polymers can be utilized on the pusher. Reinforcing elements such as braids and coils can further be used to augment stiffness along selected regions of the pusher. Once proper placement of the paravalvular leak occlusive device is confirmed, the pusher is detached from the occlusive device. The pusher and catheter are then retracted back through the femoral artery and out of the body.

Figure 12:
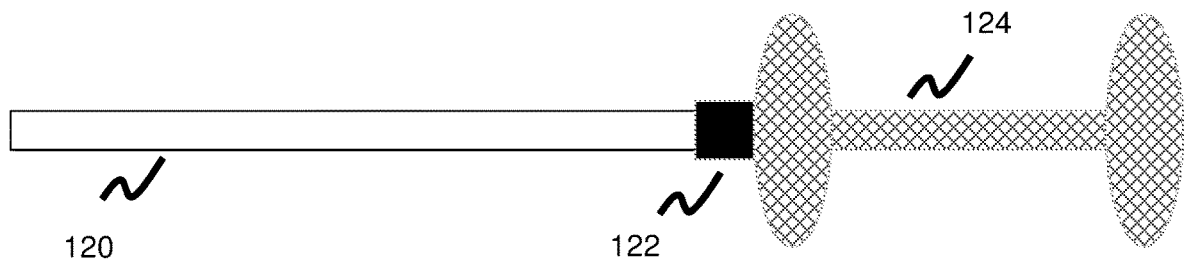
FIG. 12 illustrates a pusher delivery system for a paravalvular leak occlusive device, according to one embodiment.

The pusher/occlusive device configuration is shown in FIG. 12, where pusher 120 is connected to paravalvular occlusive device 124. A detachment junction 122 is placed between the two objects and is detachable (electrolytically, thermolytically, or mechanically) to separate occlusive device 124 from pusher 120. The occlusive device 124 adopts a first elongated, compressed configuration when within an overlying delivery catheter and a second expanded configuration (as is shown) when not within the overlying delivery catheter. In one example, the occlusive device 124 utilizes a proximal marker band (as described earlier) to connect to the detachment mechanism 122. The detachment mechanism can take on various forms including a meltable adhesive, a detachable/degradable tether, a mechanical screw-interface. In one example, the pusher utilizes a distal heater mechanism and a tether, the tether spans between the pusher and the occlusive device. The tether degrades upon application of heat to detach the occlusive device 124 from pusher 120.

Figure 13:
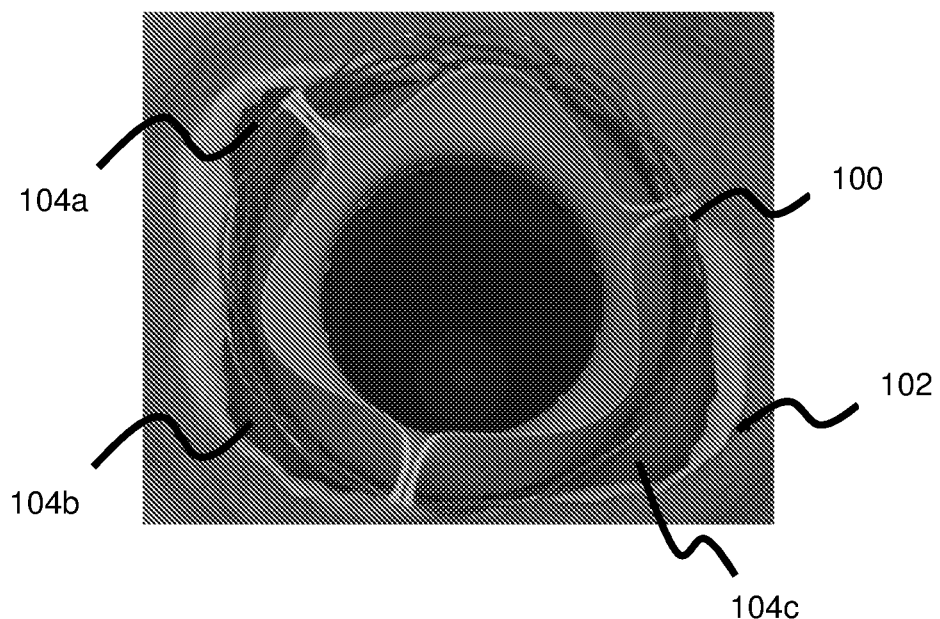
FIG. 13 illustrates a heart valve in a vessel region, according to one embodiment.

Often times the gaps between the valve and vessel can be along a plurality of sides of the valve. This is shown in FIG. 13, where a valve 100 is used in a blood vessel 102 which has an irregular shape. This irregular shape can be due for a number of reasons, including the natural anatomical shape or calcium deposits in particular locations in the vessel wall. This irregular shape makes it difficult for the valve completely fit within the vessel, and as such there are a number of gaps 104a-104c surrounding the valve 100 which can lead to paravalvular leaks. The paravalvular leak occlusive devices, discussed above, can be used to seal the gaps; however, since the gaps occur in various places spaced around the valve, a plurality of occlusive devices will be needed. One potential way to mitigate this issue is to utilize an expandable substance on the valve itself which will expand when implanted and thereby conform to the shape of the treatment region and seal any gap with the vessel.

Figure 14:
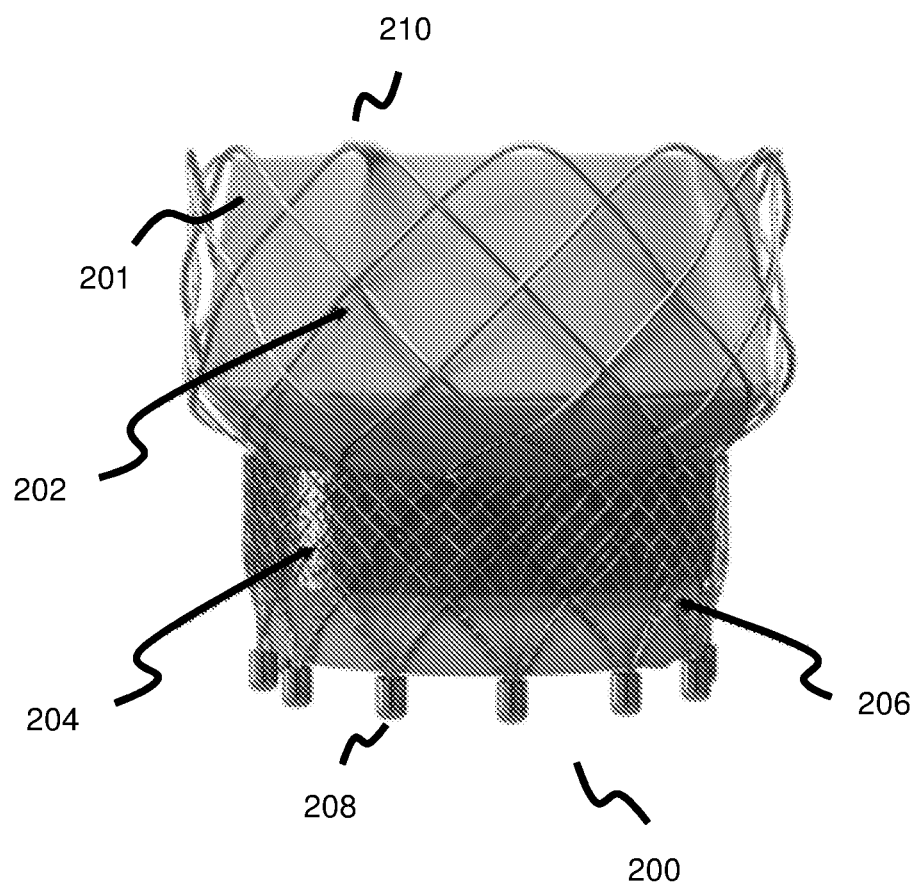
FIG. 14 illustrates a heart valve utilizing an expansile member, according to one embodiment.
Figure 15:
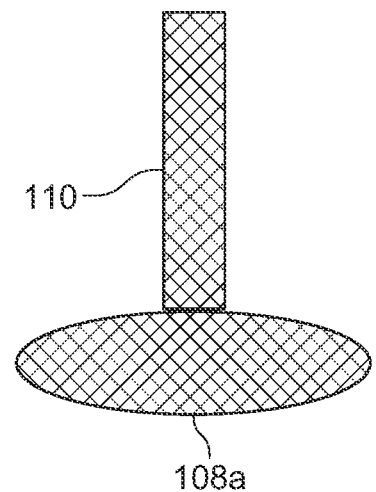
FIG. 15 illustrates a paravalvular leak occlusive device according to one embodiment.
Figure 16:
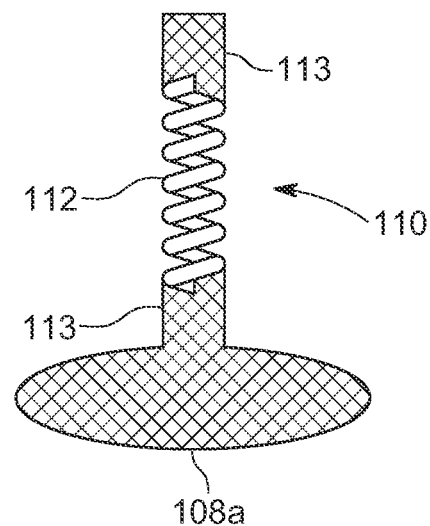
FIG. 16 illustrates a paravalvular leak occlusive device according to one embodiment.
Figure 17A:
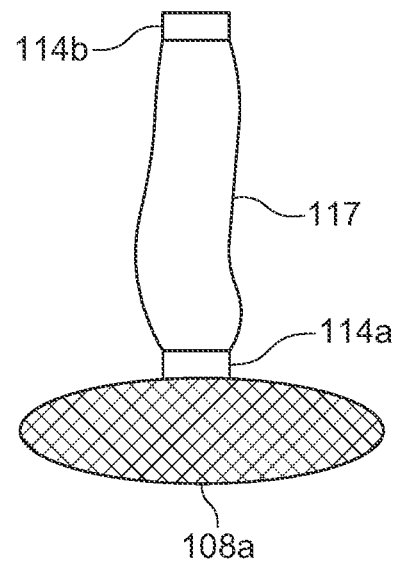
FIG. 17A illustrates a paravalvular leak occlusive device according to one embodiment.
Figure 17B:
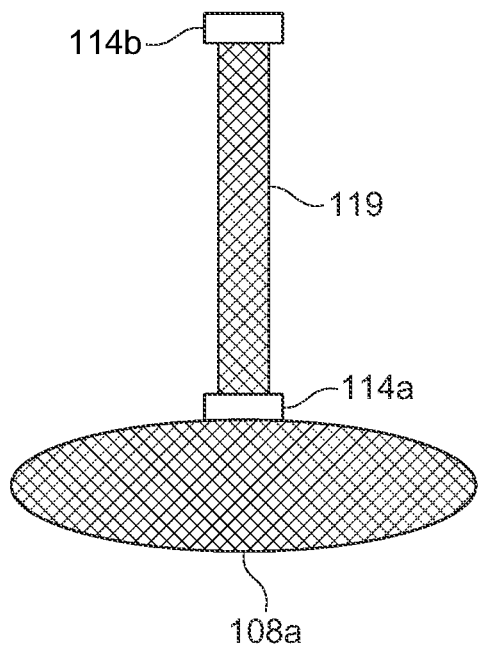
FIG. 17B illustrates a paravalvular leak occlusive device according to one embodiment.
Figure 18A:
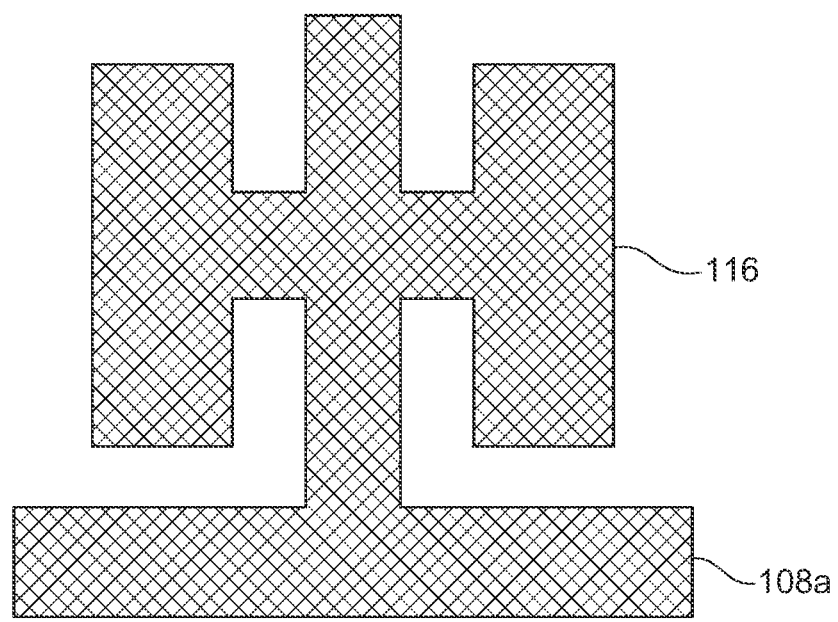
FIG. 18A illustrates a paravalvular leak occlusive device according to one embodiment.
Figure 18B:
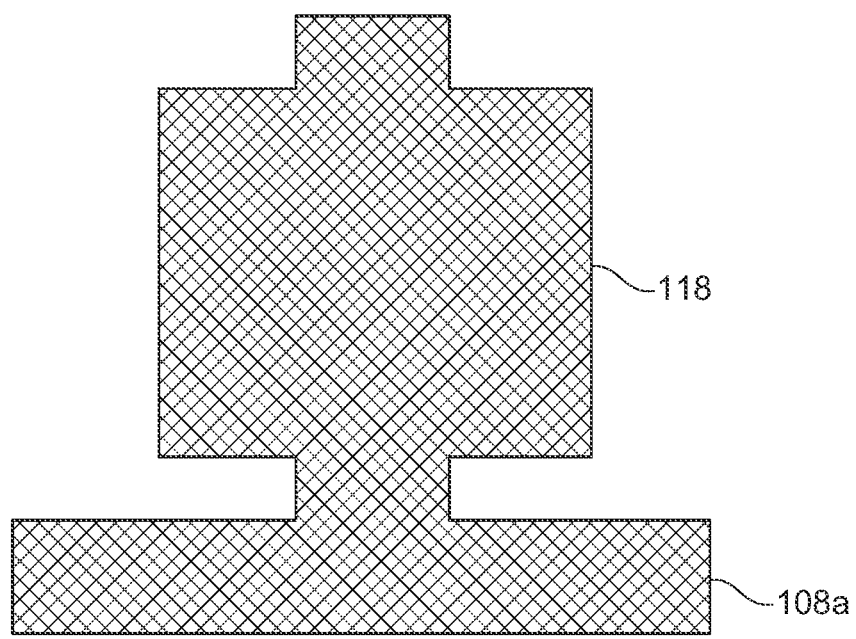
FIG. 18B illustrates a paravalvular leak occlusive device according to one embodiment.

FIG. 14 shows such a heart valve 200 utilizing an expandable member 204 around the periphery of the valve. The expandable member comprises a material that expands upon contact with blood. In one embodiment, an expansible hydrogel material is used. Hydrogels are materials that swell or expand in certain conditions. Hydrogels, when used for therapeutic purposes in the vasculature, are often configured to expand upon contact with blood; the hydrogels can be designed to expand based on reaction with blood due to the pH of blood, or due to reaction with the aqueous component of blood. Hydrogels are sometimes used on embolic coils which are used for various other occlusive purposes, such as occluding an aneurysm. The expandable material 204 is affixed to the outer surface of heart valve 200. As shown in FIG. 14, expandable material 204 is located at the lower section of the valve, however it can be located in various places on the valve depending on need. In other embodiments, the expandable material can be an EVOH or hydrogel foam. Since the expandable member/material 204 is used to seal the gaps between the heart valve and the vessel, it can also be considered a sealant, sealing member, or sealing element. As shown in FIG. 14, the expansile material 204 is placed along an inwardly recessed external region of a housing of the heart valve 200. In other embodiments, the heart valve has a more consistent housing shape which the expansile material 204 is then attached to.

A retention mechanism is needed to attach the expandable/expansile material 204 to the heart valve, so that the expandable material does not migrate. As shown in FIG. 14, the heart valve has a housing 201 containing the actual valve/gate element (not shown but within the housing 201) and an inner wire scaffold 202 is utilized on the valve housing and spans the length and breadth of the device. The lower section of the heart valve 200 contains the expandable material 204. This expansile material 204 is located in the space between the inner scaffold 202 and an outer scaffold 206 (in other words, radially between the inner scaffold 202 and outer scaffold 206); outer scaffold 206 is preferably limited to the section of the heart valve that contains the expandable material 204 so as to not increase the size profile of the heart valve too much. In other embodiments, the expansile material 204 is contained in the space between inner scaffold 202 and outer scaffold 206 in alternative ways aside from simply being placed between the inner and outer scaffold. For instance, the hydrogel could be skewered around the inner scaffold which is subsequently wrapped around the heart valve, or woven/braided into either the inner or outer scaffold. In other embodiments, the outer scaffold 206 is not used and the expandable material/sealing material 204 is attached directly to the inner scaffold 202 (e.g., through adhesives, by skewering the expansile material 204 directly to inner scaffold 202, or by weaving/braiding the material into the inner scaffold 202). Alternatively, no inner scaffold 202 is needed and just an outer scaffold 206 is used, where the outer scaffold is placed over the entirety of the valve or just the region of the valve comprising the hydrogel/expansile member 204; the expansile material 204 is placed against the valve housing 201 with the outer scaffold 206 over the expansile material 204.

The expansile materials described (hydrogels and foams) expand in the presence of blood. In some circumstances, it may be desirable to delay the expansion of the expansile/expandable material 204. For instance, early exposure to blood when the device is in the delivery catheter can prompt the expansile material to expand prematurely making delivery and deployment difficult. In some embodiments, the expandable material 204 can be acid treated to make it pH responsive or coated with a sugar or salt which gradually dissolves to expose the material to blood. Another method for delaying expansion is to run a small electrical current through the expandable material 204 to retard its expansion and then switching the current off to allow it to expand. One example of an electrical system utilizing this approach utilizes a proximal battery, one or more wires/current conveying elements along a mechanical pusher connected to the battery, where the wires connect to either the outer or inner scaffold to convey current to the expansile material 204.

The inner scaffold 202 may be made from a variety of constructions including braiding, weaving, laser cutting, etching, 3D printing, or other methods known in the art. The inner scaffold 202 can be made or wires or hypotubes made of super-elastic alloys such as nitinol, stainless steel, platinum, tantalum, chromium alloys, titanium, or DFT wires; polymers such as PEEK, PTFE, PTE, or Nylon, and/or bioabsorbable materials like polylactic acid or polyglycolic acid. These materials may be used singularly or in combination to vary the mechanical and radiopaque properties of the scaffold.

Where an outer scaffold 206 is used (not all embodiments require an outer scaffold 206 to contain the expansible material 204, as described above), it may be made with the same or similar processes/materials as described above for constructing the inner scaffold 202. In one embodiment, the outer scaffold is wound in a tighter manner compared to the inner scaffold so that the outer scaffold has smaller pores compared to the outer scaffold.

The inner scaffold 202 is attached to the valve in a variety of ways, for instance by mechanical ties or adhesive. In one embodiment shown in FIG. 14, the top part of the valve contains a plurality of extending arms 210 with a recessed receiving surface, these arms are spaced periodically around the top part of the valve. The top most end of the inner scaffold is placed within the receiving surface to connect arm 210 and inner scaffold 202. The other/bottom end of the inner scaffold has a series of caps 208, preferably composed of metal (e.g., nitinol, or tantalum/gold/platinum/palladium for visualization purposes). These caps 208 are placed over the ends of the inner scaffold braid (in one example, pairs of wire ends are affixed to cap 208; in another example, the caps are placed over the proximally projecting portion of the wire). The outer scaffold 206, located in the vicinity of the expansile material continues downwards into caps 208. The continuation of the outer scaffold beyond the immediate vicinity of the expansile material 204 will help ensure that the outer scaffold continues to retain the expansile material 204 as it expands in the vasculature; however, as discussed earlier, other embodiments can disregard the outer scaffold entirely 206 or minimize the utility of the outer scaffold if the expansile material is affixed (e.g., by skewering) directly to inner scaffold 202.

In order to maximize biocompatibility, the tissue portion of the valve is frequently made from animal tissues derived from pigs, cows, dogs, giraffes, sheep, horses, or other animals. The valve itself, which is the gate that opens and closes to regulate blood flow, may be constructed via techniques known in the art such as metallic or polymer leaflets or ball-type valves.

The embodiments shown and described in FIGS. 13-14 relate to a heart valve utilizing an expansile material 204 such as hydrogel. The expansile material (e.g., hydrogel) can also be used in the previous paravalvular leak occlusive device embodiments shown in FIGS. 5-9b to further augment the occlusive effect of the device. For instance, the medial waist region of the device can utilize a hydrogel or other expansile material to augment the expansion and occlusive effect of this section of the device. Alternatively (or additionally), the hydrogel/expansile material can be placed along the flanged ends 108a, 108b of the occlusive device, as the material expands it will provide a barrier for blood entering the gapped region through the enlarged ends 108a, 108b. The hydrogel can be placed along selected locations of the device, within the device itself, or can be skewered along part of the wire comprising the occlusive device braid. The expansile material is attached to the braid in a variety of ways, including skewering into the wire braid, mechanically affixing hydrogel to the wire braid utilizing ties or adhesive, or placing the hydrogel physically within the braid so that the braid acts like a shell.

A pusher connects to the proximal end of the heart valve to help navigate the valve through a delivery catheter, the delivery catheter is generally navigated through the femoral artery to the heart/aortic region to the valve location. The pusher can connect to the valve in a variety of ways. For instance, a connection interface such as a tether or thin wire can span between the distal part of the pusher and the heart valve; this connection interface connects to the proximal end of the heart valve or to one or more of the caps 208 at a proximal end of the valve. Various detachment means known in the art, including electrolytic, thermal, or mechanical detachment can be used to detach the connection interface from the valve to separate the pusher from the valve. Where an electrolytic or thermal concept is used, one or more wires span the entirety of the pusher to connect a proximal voltage source (e.g., battery) to the distal portion of the pusher to power the detachment mechanism. The diseased valve is either obliterated entirely or otherwise it is prepared for implantation of the replacement valve. The valve is then delivered through the arterial system (e.g., through the femoral artery) in the heart region, and the surgeon ensures the valve is positioned correctly and with the correct orientation. Heart valves are typically either self-expanding (meaning they are designed with an expanded shape memory state) or are expanded via a balloon when in the target location. The heart valve can utilize either approach, either being designed to self-expand by being made with shape memory expansile material, or it can be expanded via balloon when implanted. Once the heart valve is exposed to blood and implanted, the expansile material on the valve will expand (where the vessel wall provides a natural stop to prevent further expansion) to reduce or eliminate paravalvular leakage. As discussed above, to prevent premature expansion of the hydrogel, various techniques can be used to provide slowed expansion or timed expansion.

The invention claimed is:

1. A device to occlude a gap between a valve and a blood vessel or a tissue, comprising:
    a proximal flanged end;
    a distal unflanged end;
    a waist region connecting the proximal flanged end and the distal unflanged end, wherein the waist region has an adjustment mechanism allowing the device freedom in customizing its shape; and,
    wherein the proximal flanged end is wider than the waist region and wider than the distal unflanged end;
    wherein the adjustment mechanism includes a first region positioned between the proximal flanged end and the distal unflanged end, a second region perpendicular to the first region, and a third region parallel to the first region and positioned between the proximal flanged end and the distal unflanged end.

2. The device of claim 1, wherein the adjustment mechanism forms an H-shape.

3. The device of claim 1, wherein the device is formed from multiple braids attached together.

4. The device of claim 1, wherein the adjustment mechanism is comprised of a flexible braid or an expansile material.

5. The device of claim 1, wherein the adjustment mechanism is comprised of a hydrogel, a foam, or a fabric.

6. The device of claim 1, wherein the adjustment mechanism is comprised of a spring, a coil, a tether, or a wire.

7. The device of claim 1, wherein the adjustment mechanism is comprised of a screw or ratchet mechanism.

8. The device of claim 1, wherein the adjustment mechanism is adjacent the proximal flanged end.

9. The device of claim 1, wherein the adjustment mechanism is adjacent the distal unflanged end.

10. The device of claim 1, wherein the adjustment mechanism is between the proximal flanged end and the distal unflanged end.

11. The device of claim 1, wherein the adjustment mechanism includes a radially thicker portion and a radially thinner portion.

12. The device of claim 1, wherein the adjustment mechanism extends for an entire length between the proximal flanged end and the distal unflanged end.

13. The device of claim 1, wherein the proximal flanged end, the distal unflanged end, and the waist region form a T-shape.

14. The device of claim 1, wherein in an initial configuration the adjustment mechanism has a first shape, and wherein in an adjusted configuration the adjustment mechanism has a second shape different from the first shape.

15. The device of claim 14, wherein the first shape has a greater length than the second shape.

16. The device of claim 1, wherein the third region extends towards both the proximal flanged end and the distal unflanged end.

17. An occlusion device, comprising:
    a mesh structure having a proximal flanged end,
    a distal unflanged end, and
    a waist region therebetween, wherein the waist region has an adjustment mechanism, wherein in an adjusted configuration the waist region expands in width to include an enlarged cylindrical region having a radial width that is wider than the distal unflanged end.

18. The device of claim 17, wherein a width of the enlarged cylindrical region portion is less than a width of the proximal flanged end and greater than a width of the distal unflanged end.

19. An occlusion device, comprising:
    a proximal flanged end;
    a distal unflanged end;
    a waist region connecting the proximal flanged end and the distal unflanged end, wherein the waist region has an adjustment mechanism, wherein in an initial configuration the device has a first shape, and wherein in an adjusted configuration the device has a second shape different from the first shape, and wherein a width of the waist region is uniform along a length thereof and wherein the length of the waist region is equal to or greater than a width of the proximal flanged end.

20. The device of claim 19, wherein the proximal flanged end, the distal unflanged end, and the waist region form a T-shape.

* * * * *